US010004945B2

(12) United States Patent
Sauter (10) Patent No.: US 10,004,945 B2
(45) Date of Patent: Jun. 26, 2018

(54) TRAINING APPARATUS, ARRANGEMENT AND METHOD

(75) Inventor: Florian Sauter, München (DE)

(73) Assignee: eGym GmbH, Munich (DE)

( * ) Notice: Subject to any disclaimer, the term of this patent is extended or adjusted under 35 U.S.C. 154(b) by 371 days.

(21) Appl. No.: 13/805,455

(22) PCT Filed: Jun. 24, 2011

(86) PCT No.: PCT/EP2011/060663
§ 371 (c)(1),
(2), (4) Date: Dec. 19, 2012

(87) PCT Pub. No.: WO2012/000911
PCT Pub. Date: Jan. 5, 2012

(65) Prior Publication Data
US 2013/0095978 A1    Apr. 18, 2013

(30) Foreign Application Priority Data

Jun. 30, 2010    (EP) .................................... 10168003

(51) Int. Cl.
*A63B 24/00*    (2006.01)
*A63B 71/00*    (2006.01)
(Continued)

(52) U.S. Cl.
CPC .......... *A63B 24/00* (2013.01); *A63B 21/0058* (2013.01); *A63B 21/0059* (2015.10);
(Continued)

(58) Field of Classification Search
USPC .................................... 482/1, 8, 4
See application file for complete search history.

(56) References Cited

U.S. PATENT DOCUMENTS 4,678,248 A * 7/1987 Depenbrock ........... H02P 21/12
318/799
5,569,121 A   10/1996 Sellier
(Continued)

FOREIGN PATENT DOCUMENTS

DE    19618723       7/1997
DE    19618723 A1    7/1997
(Continued)

OTHER PUBLICATIONS

Texas Instruments Europe, "Field Oriented Control of 3-Phase AC-Motors", Feb. 1998, p. 1-24.*
(Continued)

*Primary Examiner* — Andrew S Lo
*Assistant Examiner* — Shila Jalalzadeh Abyan
(74) *Attorney, Agent, or Firm* — Hauptman Ham, LLP (57) ABSTRACT

A training apparatus including a training element for a user performing exercises, an AC motor and a frequency converter being arranged to control the AC motor, wherein the frequency converter comprises measuring means being arranged to measure a voltage and a current of the AC motor and calculation means being arranged to calculate a magnetic state of the AC motor using the measured voltage, the measured current, a reference torque and a reference flux in order to generate a torque of the AC motor. The training apparatus further comprises a control unit having a machine control module being arranged to calculate the reference flux and the reference torque using an intended overall torque, wherein the machine control module is connected to the frequency converter and arranged to transmit the reference flux and the reference torque to the frequency converter.

14 Claims, 2 Drawing Sheets

(51) Int. Cl.

| | | |
|---|---|---|
| *A63B 15/02* | (2006.01) | |
| *A63B 21/005* | (2006.01) | |
| *G06F 19/00* | (2018.01) | |
| *H02P 21/06* | (2016.01) | |
| *H02P 21/14* | (2016.01) | |
| *H02P 21/20* | (2016.01) | |
| *A61B 5/22* | (2006.01) | |
| *A63B 21/002* | (2006.01) | |

(52) U.S. Cl.
CPC ...... *A63B 24/0087* (2013.01); *G06F 19/3481* (2013.01); *H02P 21/06* (2013.01); *H02P 21/141* (2013.01); *H02P 21/20* (2016.02); *A61B 5/221* (2013.01); *A61B 5/224* (2013.01); *A63B 21/0023* (2013.01); *A63B 2071/0072* (2013.01); *A63B 2220/16* (2013.01); *A63B 2220/54* (2013.01); *A63B 2225/096* (2013.01); *A63B 2225/15* (2013.01); *A63B 2225/20* (2013.01); *A63B 2225/50* (2013.01)

(56) References Cited

U.S. PATENT DOCUMENTS

| | | | | |
|---|---|---|---|---|
| 5,585,709 | A * | 12/1996 | Jansen | H02P 6/183 318/720 |
| 5,734,249 | A * | 3/1998 | Pohjalainen | H02M 1/12 318/798 |
| 5,811,957 | A * | 9/1998 | Bose | H02P 21/34 318/802 |
| 6,094,364 | A * | 7/2000 | Heikkila | H02P 23/30 318/807 |
| 6,255,798 | B1 * | 7/2001 | Obara | B60L 11/1803 318/432 |
| 2002/0055419 | A1 * | 5/2002 | Hinnebusch | A63B 24/0084 482/8 |
| 2003/0127289 | A1 * | 7/2003 | Elgas | B60L 11/1803 187/224 |
| 2004/0070363 | A1 * | 4/2004 | Bardsley | H02P 23/08 318/727 |
| 2004/0080968 | A1 * | 4/2004 | Tarkiainen | H02P 21/0035 363/132 |
| 2006/0006836 | A1 * | 1/2006 | Miehlich | A63B 21/0058 318/807 |
| 2010/0093493 | A1 * | 4/2010 | Eldridge | A63B 21/0059 482/4 |
| 2010/0116191 | A1 * | 5/2010 | Holmberg | B66D 1/505 114/230.21 |
| 2010/0173749 | A1 * | 7/2010 | Lannon et al. | 482/8 |

FOREIGN PATENT DOCUMENTS

| | | |
|---|---|---|
| DE | 19653862 | 6/1998 |
| DE | 19653862 A1 | 6/1998 |

OTHER PUBLICATIONS

Hamid Khan, "Field Oriented Control", 2008, Renesas, p. 11, 14-16.*
K. Satyanarayana et al., "A New FOC Approach of Induction Motor Drive Using DTC Strategy for the Minimization of CMV", Jun. 2013, IJPEDS, vol. 3, No. 2, p. 241-250.*
International Search Report dated Oct. 7, 2011 for PCT/EP2011/060663.
Written Opinion of the international search authority dated Oct. 7, 2011 for PCT/EP2011/060663.
Texas Instrument Europe:"Field Orientated Control of 3-Phase AC-Motors", Technical Literature Texas Instruments Europe, Feb. 1, 1998, 18 pages.
European Office Action for application No. 10 168 003.1 dated Jan. 20, 2014.
International Preliminary Report on Patentability with Written Opinion of the International Searching Authority dated Jan. 17, 2013 for PCT/EP2011/060663.
Chinese Office Action No. 201180031989.7 dated Sep. 22, 2014.
Russian Office Action issued for Russian Patent Application No. 2013103793 dated Apr. 16, 2015.
Chinese Office Action issued for Chinese Patent Application No. 201180031989.7 dated Jun. 8, 2015.
Chinese Office Action dated May 3, 2016 for Chinese Application No. 201180031989.7.

* cited by examiner

TRAINING APPARATUS, ARRANGEMENT AND METHOD

CROSS REFERENCE TO RELATED APPLICATION

This application claims the priority of European Patent Application No. 10 16 8003.1, filed on Jun. 30, 2010 in the EPO (European Patent Office). Further, this application is the National Phase application of International Application No. PCT/EP2011/060663 filed Jun. 24, 2011, which designates the United States and was published in English.

TECHNICAL FIELD

The present invention relates to a training apparatus according to the preamble of independent claim 1. Such a training apparatus comprising a training element for a user performing exercises, an AC motor and a frequency converter being arranged to control the AC motor, wherein the frequency converter comprises measuring means being arranged to measure a voltage and a current of the AC motor and calculation means being arranged to calculate a magnetic state of the AC motor using the measured voltage, the measured current, a reference torque and a reference flux in order to generate a torque of the AC motor, can be used for Direct Torque Controlled (DTC) operation. Accordingly, this training apparatus is readily applicable to a training exercise for muscle of an exercising person. The present invention further relates to a training arrangement comprising the training apparatus, and a method for operating the training arrangement. The method enables an interactive way to support an exercising person within the exercises.

BACKGROUND ART

Training devices with electric motors for training of muscles are known in the art. For example training devices are known, wherein a computing unit supplies a frequency converter with setpoint values for the amperage and the frequency of the current of a three-phase AC motor provided for generating torque. The computing unit is supplied with the output signal of a position sensor measuring the position of a motor-driven crank which acts as a training element. By means of stored tables containing all the relevant machine-specific parameters, the computing unit calculates the values of the amperage and frequency of the motor current required for a desired course of the torque over position based on the position value of the motor-driven crank. These devices lack high accuracy necessary for a smooth training over high torque ranges.

Other training devices known in the art having a three-phase AC motor for generating torque measure two values: the speed of rotation of the motor is measured by a frequency-analogue rate sensor and the torque output is measured by a force sensor. The speed of rotation measured is used for controlling the frequency and the torque measured is used for controlling the motor current. The concept of this training device thus comprises two sensors and two interconnected control loops and its implementation therefore involves relatively high design complexity. Measuring the force by a sensor further involves potential problems such as the effects of temperature, drift as well as malfunctions resulting from vibrations or impacts.

Moreover, other training devices are known in the art having a three-phase AC motor being associated with an angle-of-rotation sensor whose measured signal is supplied to both a frequency converter and a control unit. Within these devices, the control unit provides a setpoint value for the torque to be generated by the motor and the frequency converter controls the torque by a closed control loop (comprising of the frequency converter, the AC motor and the sensor attached to the motor with its feedback to the frequency converter) using the principle of field-oriented control, also known as vector control. However, these devices have several disadvantages. First, the angle-of-rotation sensor has to detect multiple turns of the motor, as there is a reduction gear in front: This either makes the sensor a relatively complex part or additional calculations are needed to obtain the absolute position of the training element. Secondly, there is no direct information about what is happening at a motor shaft. Backlash of the gearbox and other effects after the motor shaft that might even be safety critical can hardly be detected by this design.

Further, e.g., Halabeya (High Performance Electrical Drive System for a Biomechanical Text and Rehabilitation Equipment, 2000) describes a "regular" DTC (direct torque controlled) scheme for controlling of induction motor drive within a training device used for physical rehabilitation. Such a DTC control scheme compares a reference torque and a reference flux with actual values of torque and flux. Based on this comparison control signals are produced by using a hysteresis control method. However, the reference flux is used as exclusive control value within this device in order to achieve a fast torque response time. Thus, the dosage of the torque at the motor shaft is not sufficiently precise and, further, negative effects of a high magnetization may occur. Both result in an undesirable high stiffness of the drive system, especially if the motor operates in the second or forth quadrant (i.e. "as a brake") and at low speeds. Moreover, Halabeya teaches the usage of an angular sensor mounted at the load shaft with its signal feed back to the frequency converter. The safety measure consists of four switches which are mounted near the load shaft and signal the lever bar has reached its upper or lower range of motion limits. Consequently, the device described by Halabeya does not allow detecting dangerous events like a broken link between the angular sensor and the load shaft or a malfunction within the frequency converter. Thus, the training device as described by Halabeya does not provide sufficient safeness.

There is therefore an unmet need for an improved training apparatus enabling a highly accurate responsive training resistance, safeness and quick torque response time of the motor of the training apparatus.

According to the invention this need is settled by a training apparatus as it is defined by the features of independent claim 1, by a training arrangement as defined by the features of independent claim 11, and by a method for operating the training arrangement as it is defined by the features of independent claim 13. Preferred embodiments are subject of the dependent claims.

In particular, the invention deals with a training apparatus comprising a training element for an exercising person, an AC motor and a frequency converter being arranged to control the AC motor, wherein the frequency converter comprises measuring means being arranged to measure a voltage and a current of the AC motor and calculation means being arranged to calculate a magnetic state of the AC motor using the measured voltage, the measured current, a reference torque and a reference flux in order to generate a torque of the AC motor. Such a calculation can be used within a DTC control scheme for control of the AC motor. The training apparatus further comprises a control unit having a machine control module being arranged to calculate the reference flux and the reference torque using an intended overall torque, wherein the machine control module is connected to the frequency converter and arranged to transmit the reference flux and the reference torque to the frequency converter.

In use, the training element is subject to a force exerted by the exercising person of the training apparatus during training and which may be as a non-limiting example a crank. The training element may have many different forms, such as that of a bowshaped grip, a handle or the like or of one or two pedals or a cable that is connected to the shaft by a cable winch. The scope of the present invention shall not be limited to a crank, but comprises all conceivable kinds of variants of a training element to which a person can apply muscle force. These likewise include, among other things, training elements which do not carry out a rotational but a translator motion which latter will then be mechanically converted into the rotation of a motor shaft. In this case, the terms used here for angle of rotation, speed of rotation and torque shall correspond to the terms for translatory shift or translatory speed, or force, respectively. During such exercise, the force that needs to be applied by the motor depends on a great number of parameters, including mechanical friction and inertia and of course the type of exercise the exercising person wants to perform. For this reason, the control unit calculates the reference torque and reference flux during the exercise in order to provide continuously or discontinuously the frequency converter with the calculated reference torque and reference flux. The inventive arrangement of the training apparatus allows for the provision of advantageous effects such as a quick torque response time of the AC motor in combination with a comparably precise control of the torque generated by the motor with less effort. The torque response time is particularly important at the reversal points of the exercise motion, as often changes from one direction to the other are desirable from a training perspective. Advantageously, the reference flux is adjusted as a function of the absolute amount of torque needed at an output shaft of the AC motor. This highly improves the training experience at lower torques and allows dosing the torque very precisely over a wide range and is also beneficial for the reduction of energy consumption and thus lowers the cooling requirements and allows building systems with no forced cooling but only convection cooling. This allows avoiding the noise generated by a blower.

Preferably, the machine control module splits the intended overall torque into a torque component and a flux component within the control unit, and calculates the reference flux and the reference torque based on the torque component and the flux component using a characteristic diagram. This calculation of the reference torque and reference flux within the training apparatus is particularly useful for the reduction of stiffness of the AC motor and for precise control of the torque generated by the AC motor.

Preferably, the machine control module of the control unit is arranged to calculate the intended overall torque based on a predefined training resistance provided to the control unit and a correction factor. The calculation of the intended overall torque based on the predefined training resistance and the correction factor is useful for compensating friction and mechanical inertia of the training apparatus whereby the exercises are convenient to the exercising person. The predefined training resistance can change dependent on a training lever's state of motion including its position, speed and acceleration, the predefined training resistance can change dependent on each repetition of the exercises, the predefined training resistance can change dependent on elapsed time within the exercises or the predefined training resistance can change dependent on the direction of the exercises.

As used herein, the term "predefined training resistance" relates to a weight or a level of difficulty predefined at the training apparatus or predefined otherwise as described herein below (e.g. at a web interface, at a user interface) by the exercising person wherein each effort is performed against a specific opposing force generated by resistance (i.e. resistance to being pushed, squeezed, stretched or bent). Such a predefined training resistance is used to develop the strength and size of skeletal muscles.

Preferably, the machine control module comprises a hybrid controller in order to generate the reference torque and the reference flux to the frequency converter. The hybrid controller operates before the calculation of the reference torque and reference flux takes place.

The use of a hybrid controller within the training apparatus enables a combination of multiple controllers which are switchable on the basis of discrete states, such as a state where only the torque is set and a state where the position is controlled instead as well as states that relate to safety functions. For safety reasons, the maximum speed of the motor is limited so that the training element cannot snap back with the maximum possible speed in case the exercise person releases it or slips off. Also, for safety reasons it may be expedient to limit the maximum torque of the AC motor in order to avoid the risk of overstress and the danger to sustain injuries.

Preferably, the machine control module comprises a cascade control arrangement in order to generate the reference torque and the reference flux to the frequency converter.

As used herein, the term "cascade control arrangement" relates to a control model for controlling motor drives, such as the AC motor, wherein an inner control circuit for a speed of rotation ($\omega$) and for an outer control circuit for the position (phi) is provided. Limits of phi and $\omega$ can be integrated as saturation functions within this circuit or be integrated in the frequency converter. Such a cascade control arrangement is useful for improving a reliability of safety critical measure within the training apparatus. The detailed mode of implementing this cascade control arrangement into the training apparatus is known in the art.

Preferably, the calculation means of the frequency converter comprises mathematical models for calculating the magnetic state of the AC motor. Such mathematical models are useful for the determination of the magnetic state of the AC motor and, thus, contribute to a precise control of the AC motor.

As used herein, the term "mathematical model" relates to a model in order to describe the training apparatus. In this context, mathematical models can take many forms, including but not limited to dynamical systems, statistical models or differential equations, tables or combinations thereof. These and other types of models can overlap, with a given model involving a variety of abstract structures and can be implemented to describe the training apparatus.

Preferably, the calculation means of the frequency converter comprises mathematical models for calculating rotational speed of the AC motor and temperature of the AC motor. The calculation of the rotational speed of the AC motor and the temperature of the AC motor enables a precise control of the reference torque and reference flux within the training apparatus. Further, in order to keep track of the temperature of the AC motor without using a temperature sensor, a thermal model is used to approximate the motor temperature.

Preferably, the training apparatus comprises an angular position sensor being connected to the training element, wherein the angular position sensor is arranged to sense a position of the training element and to transmit the sensed position to the control unit and wherein the control unit is arranged to adjust the reference torque and the reference flux using the sensed position.

The angular position sensor mounted to the training element, for example comprising a lever arm. The angular position sensor provides feedback of the actual motion of the lever arm to the control unit, which adjusts the reference torque and the reference flux according to the value of the angle position sensor, the rotation speed calculated by the frequency converter and a specific dataset of exercising person. Preferably, with respect to the safeness of the training apparatus, it is envisaged not to feedback the signal of the angular position sensor mounted at a lever shaft to the frequency converter, but to the higher-ranking control unit. Thus, it is possible to detect dangerous events like a broken link between the angular position sensor and the load shaft of the AC motor or a malfunction within the frequency converter.

For an efficient training and for safety reasons it is important to limit the possible range of motion of the exercising person. In order to achieve this, the control unit can vary the torque depending on the angle of the lever arm, which is measured by the angular position sensor at the lever arm, so that if a given angle is crossed, the torque increases as if there was a mechanical stop. The increasing torque might as well increase as a function of the further angular movement, so that, for instance, a mechanical spring can be simulated. In order to prevent the lever from recoiling, the additional force may depend on the direction of movement and set to zero for the direction the spring would normally expand to.

Preferably, the control unit comprises a communication module being arranged to transmit training data comprising the predefined training resistance and to obtain training data. As used herein, the term "training data" relates to data which are required before starting a training comprising personal and body-specific data, apparatus settings such as position of the exercising person, positions of fixations of the apparatus, and a training schedule comprising training goals, training methods, frequency of the training, number and order of training apparatus, frequencies of training heats, training weights. Likewise, the term "training data" relates to data which are recorded during a training comprising frequency of an exercise and exerted weight, data of the sensor signal of the angular position sensor and degree of accomplishing the training goals. Such a communication module is useful for transmitting the training data from the training apparatus, for example, to a remote database server, such as a central database server, and further for receiving training data of an exercising person.

Preferably, the communication module is arranged to be connected to a database in order to store training data in the database and to obtain training data from the database. This embodiment is, for example, useful in order to transmit a unique identification to the database which has been provided by the exercising person identifying at the training apparatus using an identification system, e.g. smart-card, contactless smart-card, finger-print detection, user identification number, personal identification number (PIN) system, barcode device, magnetic card or wireless device comprising radio frequency identification device (RFID) and bluetooth device. The database can be implemented on a local database server, on a remote database server, such as a central database server, or in the training apparatus itself. The term "database server" as used herein relates to a computer program that provides database services to other devices, modules or apparatus. Implementing the database on the training apparatus itself makes it possible to use the machine even if the network connection fails temporarily and thus improves the reliability and failure safety of the machine.

Preferably, the communication module is arranged to be connected to a network and to transmit and receive training data via the network. The communication module is useful for transmitting and receiving data over a network connection. As a non limiting example, the communication module transmits the results of training at the training apparatus to a remote database and receives data about the training of an exercising person who wants to exercise at the training apparatus.

In a further aspect of the invention, a training arrangement comprises a training apparatus as described above and a database and a web interface, wherein the database is connected to the web interface and to the communication module of the control unit of the training apparatus, wherein the web interface and the database are arranged to store or manipulate training data via the web interface. This training arrangement is useful for providing an interactive way to support the exercise person to meet his or her training goals.

Preferably, the database of the training arrangement is connected to the web interface via the World Wide Web. As used herein, the term "World Wide Web" is to be understood as a computer network consisting of a collection of formatted documents that offer data, such as training data, through the hypertext transfer protocol accessed via the Internet. The documents are formatted in a markup language called HTML (HyperText Markup Language) that supports links to other documents, as well as graphics, audio, and video files. This means it is possible to jump from one document to another by clicking on hot spots. There are several applications, like web browsers, that enable to access the World Wide Web. Accordingly, the World Wide Web is an efficient tool for exchanging data, such as training data within the training arrangement or within the training apparatus.

In another further aspect of the invention, a training arrangement comprises a training apparatus and a database and a web interface, wherein the database is arranged to be connected with the web interface and with the training apparatus.

In another further aspect of the invention, a method for operating the training arrangement comprises the steps of transmitting training data comprising the predefined training resistance to the database, manipulating the transmitted training data via the web interface, and transmitting the manipulated training data to the control unit of the training apparatus of the training arrangement.

As used herein, the term "user interface" relates to a module by which people interact with the training apparatus. Such a user interface can include hardware (physical) and software (logical) components. User interfaces exist for various devices, modules or apparatus, and provide a means of input, for example, allowing the exercising person to manipulate such devices, modules or apparatus, and/or output, for example, allowing the system to indicate the effects of the exercising persons' manipulation.

Preferably, transmitting training data within the method according to the invention comprises transmitting a predefined training resistance from the web interface to the database.

Preferably, the method further comprises the step of synchronizing data being stored in the database with a central database server, wherein the data comprises transmitted training data, manipulated training data, training data comprising a predefined training resistance.

In another further aspect of the invention, a method for operating the training arrangement according to the invention comprises the steps of transmitting training data comprising a predefined training resistance from a user interface to a database, manipulating the transmitted training data by using the web interface, and transmitting the manipulated training data to a control unit of a training apparatus of the training arrangement according to the invention.

As used herein, the term "synchronization" is to be understood within the field of computer science and refers to the need to keep multiple copies of a set of data, such as training data coherent with one another. A synchronization of data, such as training data, between the database or the remote database server such as the central database server and the web interface may be carried out either continuously or discontinuously. The synchronization of all kind of data, such as training data comprising manipulated training data, transmitted training data and training data comprising a predefined training resistance is envisaged within the method according to the invention. Thus, the synchronization of training data can occur in different ways such as between the database and the remote database server such as the central database server via World Wide Web, or between the database and the web interface being arranged to store data, or between the user interface being arranged to store data and the database and/or the remote database server such as the central database server.

Preferably, training programs are classical exercises with predefined resistance and a predefined number of repetitions and sets, or a "pyramid" training where the resistance will start at a low level, increase with the first half of repetitions and decrease with the second half of the repetitions. Also, a program for measuring the maximum strength of the exercising person is envisaged within the present invention. For this, the torque at the lever arm can be increased with the angle of the lever arm, similar to a mechanical spring, and the maximum angle the exercising person reaches is proportional to her maximum strength. As an alternative method, a lever arm can be controlled in a way to keep a fixed position by using a closed control loop. The amount of torque needed for the controller to keep this fixed position is a measure for the force the exercising person exerts on the training lever. This way, a maximum force can be measured in an isometric way. After the exercise has been finished, a set of data describing all training results is generated. Within this set of data, information about the completed repetitions, sets, weights as well as records of the sensor data are stored and transmitted over the network connection to a remote database. In turn, this database can be accessed via a database server where the gathered data and other analyses, based on this data, can be viewed by the exercising person through a website. Also, adjustments to the saved variables, e.g. the training plan, can be accomplished over the database or the central database server and will be synchronized over the network connection of the training apparatus, so that those adjustments are available the next time as soon as the exercising person identifies at the training apparatus.

BRIEF DESCRIPTION OF THE DRAWINGS

The apparatus according to the present invention is described in more detail herein below by way of exemplary embodiments and with reference to the attached non-limiting drawings, in which.

MODES FOR CARRYING OUT THE INVENTION

Figure 1:
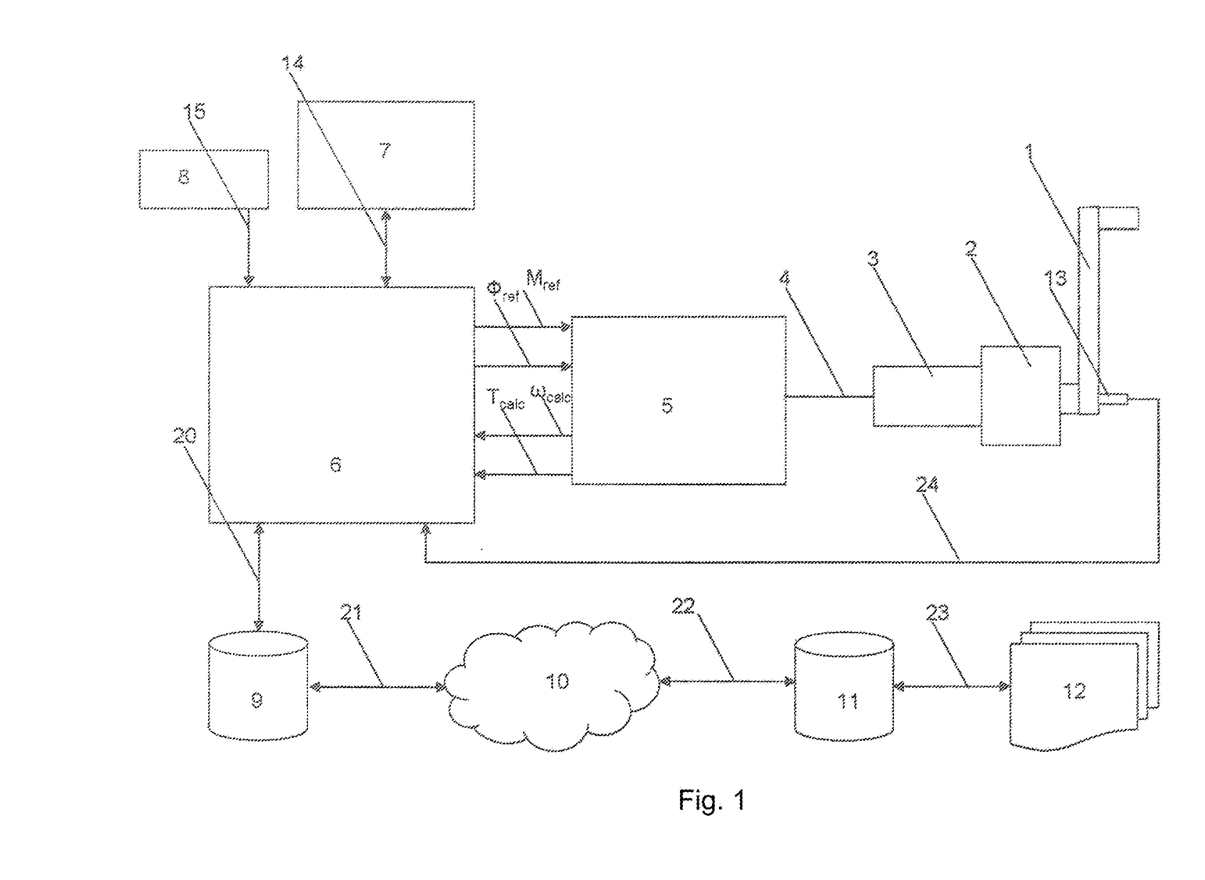
FIG. 1 shows a schematic diagram of a training apparatus according to the present invention.

FIG. 1 shows a schematic diagram of a training apparatus. The training apparatus comprises a training element 1 and an AC motor 3 which are interconnected via a reduction gearing 2. The training apparatus further comprises a frequency converter 5 being connected to the AC motor 3 via a connection 4, and a control unit 6 being connected to the frequency converter 5. The control unit 6 is also connected to an angular position sensor 13 mounted at an output shaft of the training element 1 via a data connection 24. Further, the control unit 6 is connected to a user interface 7 via a data connection 14, to an identification system 8 via a user interface connection 15 and to a database 9 via a data network connection 20. The database 9 is connected to a network 10 via a network connection 21. The network 10 is connected to a central database server 11 via a network connection 22. The central database server 11 is connected to a web interface 12 via a network connection 23.

In operation, the training element 1 is subject to a force exerted by an exercising person of the training apparatus during training. For example, the training element 1 may be in form of a crank. Further, the training element 1 may have different forms, such as that of a bowshaped grip, a handle or the like or of one or two pedals or a cable that is connected to the shaft by a cable winch.

The frequency converter 5 controls frequency, voltage and current of the three phases of the AC motor 3 in order to obtain a certain torque of the AC motor 3. Input to the frequency converter 5 is provided by the control unit 6, which provides the frequency converter 5 with values for a reference torque $M_{ref}$ and a reference flux $\phi_{ref}$. For controlling purposes, the frequency converter 5 calculates an angular rotation speed of the motor ($\omega_{calc}$) and a temperature ($T_{calc}$) and transmits it to the control unit 6. Also, the angular position sensor 13 mounted at the output shaft of the training element 1 senses the actual position of the training element and forwards the signal to the control unit 6. Additionally, the identification system 8 enables to exercise person to identify at the training apparatus. The identification system 8 comprises smart-card, contactless smart-card, finger-print detection, user identification number, personal identification number (PIN) system, barcode device, magnetic card or wireless device comprising radio frequency identification device and bluetooth device. A unique identification is then sent from the user identification system 8 to the control unit 6 via the user interface connection 15. For further interaction, the user interface 7 is provided which gets data via the data connection 14 and transmits the exercising person's input signals via the data connection 14 back to the control unit 6. In one embodiment, the user interface 7 is a device having a touch-screen for entering and displaying training data. The control unit 6 is equipped with the data network connection 20. Through this connection, training data is exchanged with the database 9 which itself is connected with the network 10, e.g. the World Wide Web, via the network connection 21. The training data can be viewed and settings for the training apparatus can be manipulated by the use of the web interface 12. The training data is synchronized between the central database server 11 and the database 9. The database 9 and/or the central database server 11 are/is connected to the web interface 12 and to the training apparatus, wherein the web interface 12 and The database 9 and/or the central database server 11 are arranged to store or manipulate training data via the web interface 12. Preferably, the angular rotation speed of the AC motor 3 is not measured with a sensor but calculated within the frequency converter using a mathematical motor model. Further, the direct torque control scheme for the AC motor 3 is implemented within the frequency converter 5. With direct torque control, both, flux and torque are controlled by a hysteresis controller which makes the controller very responsive and the advantages of a DC motor like direct control of the torque and direct control of the flux can be transferred to the AC motor 3. Thus, the need of an encoder at the motor is eliminated.

Figure 2:
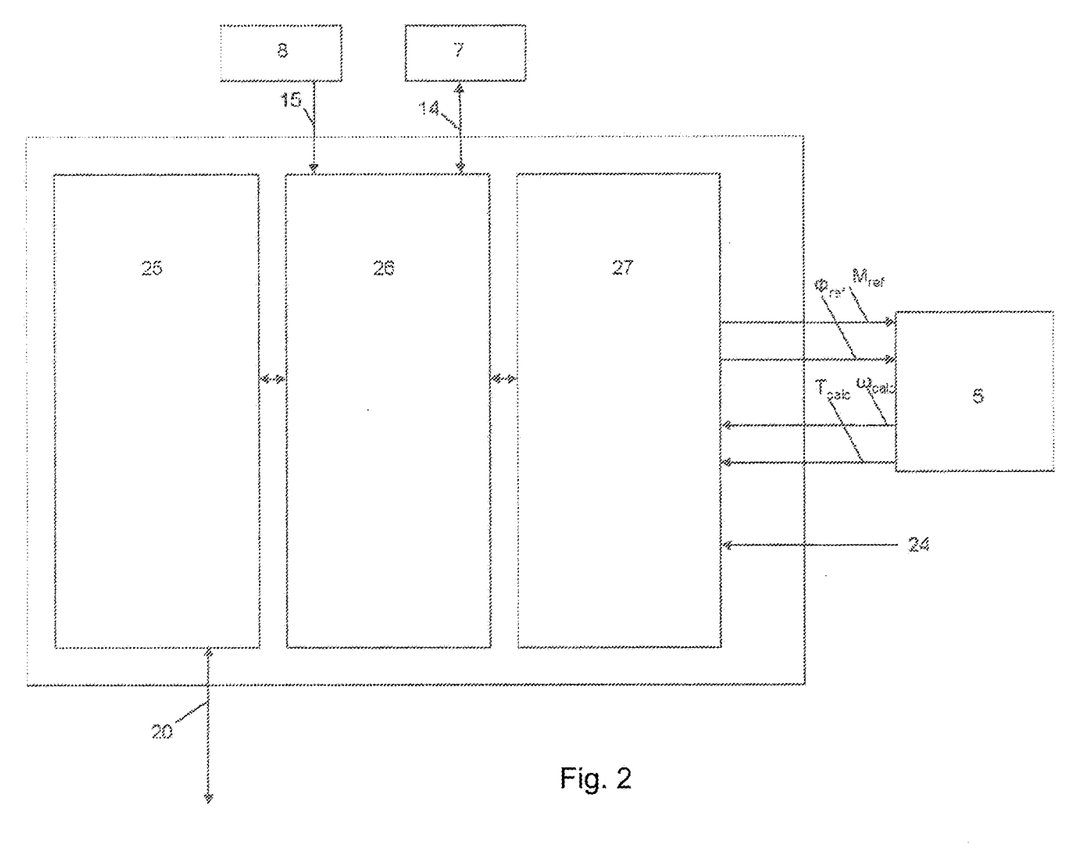
FIG. 2 shows a schematic diagram of a control unit of the training apparatus from FIG. 1.

FIG. 2 shows a schematic diagram of the control unit 6 of the training apparatus from FIG. 1. The control unit 6 comprises a communication module 25, a user interface module 26 and a machine control module 27. Preferably, the communication module 25 is connected to the network connection 20 and to the user interface module 26, which is further connected to the machine control module 27. The data connection 24 is associated to the machine control module 27. The user interface module 26 is further connected to the identification system 8 via the user interface connection 15 and to the user interface 7 via the data connection 14. The data network connection 20 is associated to the communication module 25.

Preferably, the communication module 25 transmits and receives data over the network connection 20, especially it transmits the results of a training at the training apparatus to a database 9 via the data network connection 20 and, further, receives data about the training of an exercising person who wants to exercise at the training apparatus. This data may contain information about the weights, the repetitions and the number of sets as well as training apparatus—specific settings like the position of fixations or the seat position or information about the training mode or historical training data of the exercise person.

The control unit 6 further comprises the user interface module 26 receiving identification data of the exercising person from the identification system 8 via the user interface connection 15 and provides information to the exercising person. The exercising person interacts with the user interface 7 via the data connection 14. The inputs are forwarded to the user interface module 26 and processed there.

The control unit 6 further comprises the machine control module 27. Particularly, the machine control module 27 calculates the setpoint values for the reference torque and the flux reference. In order to generate those values, two advantageous principles may be used. One possibility is an implementation of a cascade control arrangement, i.e. an inner control circuit for the speed of rotation ω and an outer control circuit for the position phi. Limits of phi and ω can be integrated as saturation functions within this circuit or be integrated in the frequency converter in order to improve the reliability of the safety critical measure. Alternatively, a hybrid controller may be used being implemented within the machine control module 27.

The hybrid controller possesses different discrete states, i.e. a state where only the torque is set and a state where the position is controlled instead as well as states that relate to safety functions. Within the states, the controller acts as a continuous controller but on external events the discrete states can be changed. For example, crossing an upper limit of the speed ω triggers a signal that sets the controller to a state that deals with this problem until it is solved and switches back to another state then.

In the following a possibility of carrying out the invention is presented: In order to know for the training apparatus, which training program to perform, an exercising person identifies at the training apparatus. The user interface module 26 is connected to the identification system 8 which enables the exercising person to identify at the training apparatus using an identification mean, such as a smart-card, contactless smart-card, finger-print detection, user identification number, personal identification number (PIN) system, wireless device comprising radio frequency identification device, bluetooth device, barcode device or magnetic card. A unique identification is sent to the control unit 6 via the user interface connection 15. The control unit 6 is arranged to transmit a unique identification to the database 9 and the central database server 11. The database 9 and the central database server 11 allot the unique identification to data being subsequently transmitted to the control unit 6. The training data comprise data about the exercising person, i.e. name, and training apparatus settings, i.e. position of the exercising person, position of the fixations or of the mechanical end stop, and information on the training schedule, meaning information on the exercise allotted to the training apparatus such as training weight, frequency of the exercise, speed of the exercise and a pointer to the upcoming exercise. Particularly, within this set of data, a training schedule is stored, comprising all possible information about the training, including for which period of time the training schedule is valid, how often the exercises should be conducted, which training apparatus is involved in which order, which breaks should be held between sets and training apparatus, how fast the motion of the exercise should be conducted, which mechanical positions (e.g. of the seat) should be set and how the training weight will vary either with the training angle, the repetition count or the set count or a combination of all of these factors and how the range of motion should be set.

The control unit 6 adjusts settings of the training apparatus based on the data provided by to the database 9 and/or the central database server 11 in order to activate a training course, like power training with constant training weight and a defined frequency of the exercise. Subsequently, the control unit 6 transmits the data such as reference torque and reference flux to a frequency converter 5 and, thus, the training course is started. The control unit 6 adjusts a position of a training lever based on the provided data about the exercising person via a feedback signal of an angular position sensor 13 to an individual initial setting.

If the training lever will be slightly raised, the control unit 6 calculates an intended overall torque which is arranged to be calculated based on a predefined training resistance provided to the control unit 6 and a correction factor, wherein the control unit 6 comprises the machine control module 27 being connected to the frequency converter 5 and arranged to transmit the reference flux and the reference torque to the frequency converter 5.

A force that needs to be applied by the motor during the exercise depends on a great number of parameters, including mechanical friction and inertia and of course the type of exercise the exercising person wants to perform. For this reason, the control unit 6 calculates the reference torque and reference flux during an exercise in order to provide the frequency converter 5 with the calculated reference torque and reference flux. Additionally, the control unit 6 analyses the data provided by the angular position sensor 13 during an exercise. This analysis provides information on whether the exercising person fulfils the presetting of a training schedule. This information will be provided to the exercising person via the user interface 7.

After finishing the exercise, the control unit 6 adjusts the training lever to the initial position. All data gathered during the exercise is transmitted to and stored to the database 9 and the central database server 11 via the communication module 25. The exercising person is informed about the upcoming exercise via the user interface 7.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the Figures individually although they may not have been described in the afore or following description. Furthermore, in the claims the word "comprising" does not exclude other elements or steps, and the indefinite article "a" or "an" does not exclude a plurality. A single step may fulfil the functions of several features recited in the claims. The terms "essentially", "about", "approximately" and the like in connection with an attribute or a value particularly also define exactly the attribute or exactly the value, respectively. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A training apparatus, comprising:
an AC motor having an output shaft;
a training element to which an exercising person is to apply force, the training element connected to the output shaft of the AC motor;
a frequency converter connected to the AC motor and configured to
control the AC motor by using a direct torque control (DTC) scheme,
measure a voltage and a current of the AC motor, and
calculate a magnetic state of the AC motor using the measured voltage, the measured current, a reference torque and a reference flux in order to generate an intended overall torque of the AC motor, wherein the generated intended overall torque is transmitted to the training element to enable the exercising person to exercise against the generated intended overall torque; and
a control unit comprising a machine control module connected to the frequency converter and configured to
calculate the reference flux and the reference torque using the intended overall torque, by
splitting the intended overall torque into a torque component and a flux component, and
calculating the reference flux and the reference torque based on the flux component and the torque component, respectively, using a characteristic diagram, wherein the reference flux is adjusted as a function of an absolute value of the intended overall torque needed at the output shaft of the AC motor, and
transmit the reference flux and the reference torque to the frequency converter,
wherein the machine control module is further configured to calculate the intended overall torque at least based on a predefined training resistance provided to the control unit.

2. The training apparatus according to claim 1, wherein the machine control module is further configured to calculate the intended overall torque further based on a correction factor.

3. The training apparatus according to claim 2, wherein the control unit comprises:
a communication module configured to transmit training data comprising the predefined training resistance, and obtain training data.

4. The training apparatus according to claim 3, wherein the communication module is further configured to
be connected to a database,
store training data in the database, and
obtain training data from the database.

5. The training apparatus according to claim 3, wherein the communication module is further configured to
be connected to a network,
transmit and receive training data via the network.

6. The training apparatus according to claim 1, wherein the machine control module comprises a hybrid controller configured to calculate the reference torque and the reference flux.

7. The training apparatus according to claim 1, wherein the frequency converter comprises mathematical models for calculating the magnetic state of the AC motor.

8. The training apparatus according to claim 1, comprising an angular sensor being connected to the training element,
wherein the angular sensor is configured to sense a position of the training element and transmit the sensed position to the control unit, and
wherein the control unit is configured to adjust the reference torque and the reference flux using the sensed position.

9. The training apparatus according to claim 1, wherein the machine control module is further configured to calculate the reference flux and the reference torque by additionally using a hysteresis control method.

10. A training arrangement, comprising:
the training apparatus according to claim 3;
a database; and
a web interface,
wherein the database is connected to the web interface and to the communication module of the control unit of the training apparatus, and
wherein the web interface and the database are configured to store and/or manipulate training data via the web interface.

11. The training arrangement according to claim 10, wherein the database is connected to the web interface via the World Wide Web.

12. A method for operating the training arrangement according to claim 10, the method comprising:
- transmitting training data comprising the predefined training resistance to the database;
- manipulating the transmitted training data via the web interface; and
- transmitting the manipulated training data to the control unit of the training apparatus of the training arrangement.

13. The method according to claim 12, wherein transmitting training data comprises transmitting the predefined training resistance from the web interface to the database, or from a user interface of the control unit of the training apparatus.

14. The method according to claim 12, further comprising:
- synchronizing data being stored in the database with a central database server,
- wherein the data comprises transmitted training data, manipulated training data, and training data comprising the predefined training resistance.

* * * * *